United States Patent
Christou et al.

(10) Patent No.: US 6,492,526 B1
(45) Date of Patent: Dec. 10, 2002

(54) DIVALENT LANTHANIDE METAL COMPLEXES

(75) Inventors: Victor Christou, Oxford (GB); Oleg Victorovitch Salata, Oxford (GB); Christopher Shipley, East Yorkshire (GB)

(73) Assignee: Isis Innovation Limited (GB)

( * ) Notice: Subject to any disclaimer, the term of this patent is extended or adjusted under 35 U.S.C. 154(b) by 0 days.

(21) Appl. No.: 09/787,965

(22) PCT Filed: Sep. 24, 1999

(86) PCT No.: PCT/GB99/03201

§ 371 (c)(1),
(2), (4) Date: Jul. 31, 2001

(87) PCT Pub. No.: WO00/18851

PCT Pub. Date: Apr. 6, 2000

(30) Foreign Application Priority Data

Sep. 25, 1998 (GB) ............................................. 9820805

(51) Int. Cl.$^7$ .............................. C07F 5/00; B32B 9/00; H01J 63/04
(52) U.S. Cl. ..................... 548/101; 548/109; 534/15; 313/503; 313/506; 428/690; 428/917
(58) Field of Search ................................. 548/101, 109; 534/15; 313/503, 506; 428/690, 917

(56) References Cited

U.S. PATENT DOCUMENTS 6,083,634 A * 7/2000 Shi .............................. 428/690

FOREIGN PATENT DOCUMENTS

WO WO 98/55561 12/1998
WO WO 98/58037 12/1998

OTHER PUBLICATIONS

Domingos et al., Polyhedron, vol. 14, No. 20–21, pp. 3067–3076 (1995).*
X. Zhang et al., "Synthesis and structure of the first bis–hydrotris(3–$^t$Bu–5–Me pyrazolyl)borate complexes, Ln(Tp$^{tBu,Me}$)$_2$ (Ln=Sm, Yb): fluxionality, bonding mode exchange and B–H–Ln bridge bonding," *New J. Chem.* (1995), vol. 19, pp. 573–585.
T. Sano et al., "Novel Europium Complex for Electroluminescent Devices with Sharp Red Emission," *Jpn. J. Appl. Phys.*, Part 1 (1995), vol. 34(4A), pp. 1883–1887, XP–002127017.
Michael A. J. Moss et al., "Polypyrazolylborate Derivatives of the Lanthanides, the Syntheses of Oxidation State(II) Complexes," *Polyhedron* (1993), vol. 12, pp. 1953–1955, XP–002127018.
J. Takats, "Hydrotis(pyrazolyl)borates. Versatile ligands for f–element complexation," *Journal of Alloys and Compounds* (1997), vol. 249, pp. 52–55.

* cited by examiner

Primary Examiner—Porfirio Nazario-Gonzalez
(74) Attorney, Agent, or Firm—Lahive & Cockfield LLP; Anthony A. Laurentano; Peter C. Lauro

(57) ABSTRACT

Organometallic complexes comprising a divalent lanthanide metal cation complexed with from one to three polydentate ligands which preferably contain one or more pyrazolyl groups, such as trispyrazolylborate anions, are useful in light emitting devices e.g., in electroluminescent flat panel displays.

In the complexes, several classes of which are novel, the lanthanide metal is preferably Eu since the Eu complexes have the ability to exhibit bright electroluminescence ranging from yellow to orange to blue.

23 Claims, 2 Drawing Sheets

DIVALENT LANTHANIDE METAL COMPLEXES

This invention relates to divalent lanthanide metal complexes, to processes for their preparation and to light emitting devices containing the complexes.

Flat panel displays are the critical enabling technology for many current applications, including laptop computers and "head up" displays, as they offer several potential advantages over conventional cathode ray tube displays, including compactness and low power consumption.

Currently, the flat panel display market is dominated by liquid crystal technology, but these materials suffer several drawbacks including small operational viewing angles, poor image contrast and high power consumption. As an alternative technology for flat panel displays, electroluminescent (EL) displays using semiconducting organic polymers offer the potential of lower cost, improved viewing angles, better contrast and lower power consumption. However, these materials often have broad emission profiles, resulting in poor chromaticity and reduced device efficiency.

Typically, a flat panel device is a multilayer assembly of structurally important films consisting of a transparent electrode, insulation, phosphor and metal electrode. All are important materials in device fabrication, but the single most important element in the development of a multi-colour electroluminescent device is the phosphor.

It is known that organometallic complexes can be used as phosphors in electroluminescent devices. For example, U.S. Pat. No. 5,552,547 describes complexes of aluminium, gallium and indium in which one of the ligands acts as a "built-in" fluorescent dye. The colour of the light which is emitted from the complex is determined by the ligand which acts as the dye.

Lanthanide-based materials are gaining popularity as phosphors for thin film devices, as they offer several potential advantages over other light emitting species: such as narrow emission linewidths, the potential for device structures with efficiencies greater than 25% and excellent Commission Internationale de I'Eclairage (CIE) colourmap coordinates. To date, two distinct types of lanthanide metal based phosphors have been reported in the literature; those based upon solid-state inorganic matrices doped with small amounts of the lanthanide ion and molecular coordination complexes. Conventional inorganic thin film EL devices are based upon solid-state phosphors and this group of materials are amongst the most extensively studied of all EL devices in the literature. Unfortunately, these solid-state devices, often based on doped II-VI materials, require large driving voltages and this has hampered their development in portable thin film displays, although there are reports of adequately functioning thin film structures. Recently, several groups of workers have recognised the potential of molecular organometallic phosphors to incorporate the processing and manufacturing advantages of organic materials with the emissive properties of the solid-state materials and reports of the use of lanthanide coordination complexes as hybrid materials are becoming increasingly common. To date these devices have been based almost exclusively upon trivalent europium (red emitting) and terbium (green emitting) complexes with bidentate oxygen donor ligands such as benzoylbenzoate and acetylacetonate derivatives.

M. A. Pavier et al., Thin Solid Films, 284–285 (1996) 644–647, describe electroluminescence from dysprosium- and neodymium-containing Langmuir-Blodgett films. The metal is in the trivalent state in the complexes and the ligand used is a pyrazolone-based molecule in which the binding to the metal by the ligand occurs via a beta-diketonate-type arrangement.

The trivalent europium complex with phenanthroline and thenoyltrifluoroacetone is disclosed in Sano et al, *Jpn. J. Appl. Phys.*, vol.34 (1995), p. 1883–1887 and Campos et al in *J. Appl. Phys.*, vol.80, no.12 (1996), p. 7144–7150. Both Sano et al and Campos et al teach the use of the complexes to provide red light in electroluminescent devices. Like the complexes disclosed by Pavier et al, it is the beta-diketonate part of the ligand which binds to the metal.

The synthesis and structure of bis(tris(3,5-dimethtylpyrazolyl)borate)samarium (II) is described by Takats et al in *Organometallics* 1993, 12, 4286–4288. However, there is no mention of the light emitting properties of the compound, only its structure and that of its reaction product with azobenzene. The syntheses and structures of the compounds bis[hydrotris(3-tert.butyl-5-methylpyrazolyl) borato]samarium and bis[hydrotris(3-tert.butyl-5-methylpyrazolyl) borato]ytterbium are described by Zhang et al. in New J. Chem. 1995. 19. 573–585. Certain bis- and mono-hydrotris(pyrazolyl)borate complexes of samarium and ytterbium are also described by J. Takats, J. Alloys and Compounds 249 (1997) 52–55.

Light emitting devices containing lanthanide (III) complexes are described in WO 98/06242. Trispyrazolylborate complexes of non-lanthanide metals are also mentioned but only as electron transporting hosts for phosphors. There is no mention of the use of trispyrazolylborate complexes as phosphors, of complexes of these ligands with lanthanide metal ions or of lanthanide (II) complexes at all.

One of the problems associated with the optical emissions from the trivalent lanthanide metal ions is that they are dominated by the relatively weak spin forbidden f—f transitions. Also, the wavelength of the emission from these transitions is generally independent of the ligand in the complex and is therefore difficult to tune by altering the nature of the ligand. The present invention solves these problems by providing a new class of lanthanide metal complexes for use as phosphors in light emitting devices in which the lanthanide metal is in the +2 oxidation state i.e., it is divalent.

Accordingly, the present invention provides a light emitting device comprising a complex containing a divalent lanthanide metal cation complexed with from one to three polydentate ligands.

Unlike the emissions from the trivalent lanthanide metal ions, emissions from the metal in the divalent state may arise from both inter-shell transitions between the $4f^6 5d^1$ excited state and the $4f^7$ ground state and charge transfer (CT) transitions, both of which are quantum mechanically allowed and therefore potentially very efficient. Furthermore, unlike the f—f transition of trivalent species, the wavelength of the emission is ligand-dependent and, therefore, potentially tunable. Emission linewidths are also broadened since the transition is affected by differences in metal-ligand bond lengths between the ground and excited states of the molecule.

Preferably, each ligand in the complexes of the invention comprises one or more pyrazolyl groups, optionally substituted and optionally fused with a substituted or unsubstituted, heterocyclic or carbocyclic, aromatic or non-aromatic, ring system, and one of the nitrogen atoms of the pyrazolyl groups forms a coordinate bond to the metal. More preferably, each ligand is a trispyrazolylborate anion, the pyrazolyl groups each being optionally substituted and optionally fused with a substituted or unsubstituted, heterocyclic or carbocyclic, aromatic or non-aromatic, ring system, optionally substituted at the boron atom.

Suitable complexes for use in the invention are desirably those having the formula (I):

$$[(Z(L)_3)_p M] A_q \qquad (I)$$

wherein

Z is a carbon atom or $R^1$—B fragment p is 1 or 2 q is 2-p

A is a counterion $R^1$ is: (i) hydrogen, aryl or aralkyl each optionally substituted with from one to five halogen or $C_1$ to $C_6$ alkyl groups; or (ii) $C_1$ to $C_6$ alkyl, $C_2$ to $C_6$ alkenyl or $C_2$ to $C_6$ alkynyl each optionally substituted with one or more halogen atoms each L is covalently bound to Z and is independently selected from a group of the formula (II) or (III)

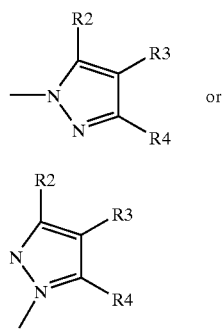

in which $R^2$, $R^3$ and $R^4$ are independently selected from: (i) halogen, cyano, nitro, sulphono, amino, $C_1$ to $C_6$ alkylamino, $C_1$ to $C_6$ alkylamido, carboxyl, $C_1$ to $C_6$ alkyloxycarbonyl, hydroxy, $C_1$ to $C_6$ alkoxy, $C_1$ to $C_6$ alkylcarbonyloxy, $C_1$ to $C_6$ alkylcarbonyl $C_1$ to $C_6$ haloalkoxy and hydrogen; (ii) aryl or aralkyl each optionally substituted on the aryl ring or, for aralkyl, on the alkylene chain with from one or more of the groups mentioned under (i) above; and (iii) $C_1$ to $C_6$ alkyl, $C_2$ to $C_6$ alkenyl or $C_2$ to $C_6$ alkynyl each optionally substituted with one or more of the groups mentioned under (i) and (ii) above or either $R^2$ and $R^3$ or $R^3$ and $R^4$ are linked so as to form a fused, aromatic or non-aromatic, ring system with the pyrazolyl ring of L and M is a divalent lanthanide metal ion selected from Eu, Sm and Yb. p is preferably 2.

The light emitting device of the invention may be a flat panel display.

A number of the complexes of formula (I) are believed to be novel and are also provided by the invention.

The term "alkyl" as used herein is intended to cover branched and unbranched $C_1$ to $C_6$ groups and alicyclic compounds for the $C_3$ to $C_6$ groups. The terms "alkenyl" and "alkynyl" are intended to cover branched and unbranched $C_2$–$C_6$ groups which contain one or more unsaturated C=C bonds or C≡C bonds, respectively.

The term "aryl" covers $C_6$ to $C_{10}$ aromatic groups such as phenyl and naphthyl as well as heterocycles such as pyridyl, furyl and thiophenyl. The term "aralkyl" means $C_1$ to $C_3$ alkyl substituted with aryl, such as benzyl.

The term "halogen" means fluorine, chlorine, bromine or iodine. Of these, fluorine is the preferred halogen for the complexes of the invention.

M is Eu (europium), Sm (samarium) or Yb (ytterbium) since of all the lanthanide metals these three form the most stable divalent compounds and complexes. The Eu complexes of the invention are particularly preferred on account of their ability to exhibit bright electroluminescence which, as disclosed herein, may range from yellow to orange to blue.

The trispyrazolyl ligands used in the invention have been found to be particularly effective in terms of their sensitising efficiency i.e., in transferring energy to the metal in the excitation step of the light emitting (e.g., electroluminescence) process. They also impart high radiative efficiencies to the complexes by providing few non-radiative pathways for relaxation (i.e., energy loss from the metal in its excited state). Some of these ligands have been reported. Dias et al, *Inorg Chem,* 1995, 34, 1975 and 1996, 35, 267 and Renn et al *Helv Chim Acta* (1995), 78, 993 describe the synthesis of the fluorinated trispyrazolyl borate ligands. Julia et al., Organic Preparations and Procedures International, 16, 299, 1984, discloses the preparation of the trispyrazolylmethane-derived ligands. The conventional synthetic routes to these complexes offer further advantages for light emitting devices in that these materials are prepared in rigorously anaerobic and anhydrous conditions and thus water and oxygen are excluded from the device preparation at all stages. This is beneficial, since water is known to quench photoluminescence in molecular species and both oxygen and water have a deleterious effect upon the properties of light emitting devices.

The complexes of the invention are generally called "organometallic" herein. However, it will be understood by those skilled in the art that this term is used synonymously with the term "coordination". Also, the term "complex" as used herein covers both neutral species and compounds containing a charged organolanthanide species as part of a complex salt.

The light emitted from the light emitting devices of the invention may be produced by various mechanisms such as electroluminescence, photoluminescence or cathodoluminescence with electroluminescence being preferred.

In the light emitting devices of the invention, the complexes may be provided as a thin film of the complex itself or in the form of a dispersion of the complex in a polymer matrix. When a matrix is used, it is preferably of the type conventionally used in light emitting (e.g., electroluminescent) devices and based on polymer systems such as polyvinylcarbazole (PVK) or polymethylmethacrylate (PMMA) with a hole transporting material such as 2-(4-biphenylyl)-5-(5-tertbutylbenzene)-1,3,4-oxadiazole (BBO). The organolanthanide complexes used in the invention may themselves act as electron transporting materials, separately from or in addition to being a phosphor, in the light emitting devices.

The ligands $ZL_3$ used in the complexes of formula (I) of the present invention in which $R^4$ and/or $R^2$ is —$(CX_2)_n X$ or optionally substituted orthodihalogenated or orthodiperhalomethylated aryl are particularly advantageous for use in the light emitting device of the invention since they provide complexes with no carbon-hydrogen (C—H) bonds within 5 Å (0.5 nm) of the metal centre. Keeping C—H bonds away from the metal centre reduces the number of non-radiative pathways for relaxation of the complexes and thus increases their light emitting efficiency.

In the complexes of formula (I), $R^4$ and/or $R^2$ is conveniently trifluoromethyl. Also, $R^4$ and $R^2$ may both be methyl. $R^3$ may be hydrogen and $R^2$ trifluoromethyl. According to one particular embodiment of the invention the organometallic complex has the formula I above in which Z is H—B and at least one of the L groups is a pyrazolyl group having the formula II or III above in which at least one of $R^2$, $R^3$ and $R^4$ is a trifluoromethyl group. Preferably, in each L group one of $R^2$ and $R^4$ is a trifluoromethyl group and the other is selected from $C_1$–$C_6$ alkyl, $C_2$–$C_6$ alkenyl, $C_2$–$C_6$ alkynyl, aryl and aralkyl, as defined above, and $R^3$ is H. A specific example of such a complex has the formula

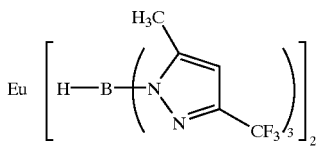

This specific complex, which exhibits bright blue luminescence under UV irradiation, belongs to a subclass of europium compounds of formula I having at least one trispyrazolylborate ligand containing $CF_3$ and other ring substituents which may have use as electroluminescence phosphors. The natures of the other variable substituent groups on the pyrazolyl rings act to tune the properties of the complex, such as volatility, solubility and hole and electron transporting properties. It is also found that the presence of the trifluoromethyl substitutents has a protecting effect on the Eu ion thus rendering the complexes stable to air and moisture, even on exposure for several weeks.

As an alternative to the above, $ZL_3$ may be:

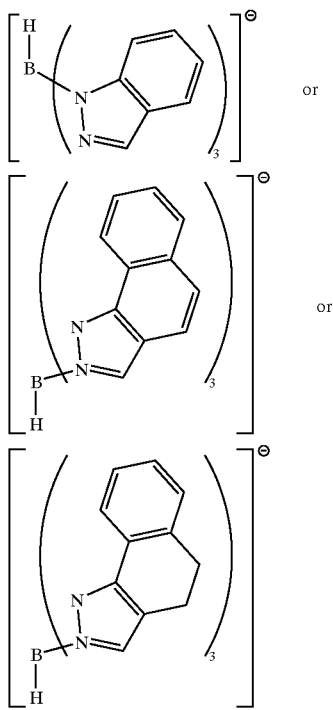

The increased conjugation of the fused bi- and poly-cyclic systems can be advantageous for electron transfer within the complex.

The complexes of formula (I) preferably have p equal to 2 and q equal to zero so that they are neutral overall. Neutral complexes are particularly useful since they are relatively readily vaporised and thus are easy to purify and to deposit as a thin film (e.g., in the light emitting device). However, where the complexes used in the invention are positively charged, they will be provided by compounds containing the complex and a counterion. The counterion preferably should not provide non-radiative pathways for relaxation of the metal. Therefore, it is preferred that the counterion should not contain bonds between hydrogen and other atoms, such as carbon-hydrogen bonds. Trifluoromethylsulphonate, $CF_3SO_3^-$, halide (fluoride, chloride, bromide or iodide), nitrate, $NO_3^-$, and perchlorate, $ClO_4^-$, are suitable counterions for this purpose.

In yet another embodiment, the present invention provides a process for producing the complex of the invention, as defined in formula (I), which comprises the steps of reacting $M^{2+}$ ions (i.e., divalent lanthanide ions) with $ZL_3$ anions in solution and separating the complex from the reaction mixture. The process is carried out in a suitable solvent (e.g., an aprotic solvent such as THF) at about or above room temperature up to the boiling point of the solvent for a time sufficient to form a suitable amount of the complex, preferably with stirring. Where the complex is insoluble in the solvent for the reaction, it may be separated from the reaction mixture by filtration and then, where it is neutral, purified by sublimation (preferably at reduced pressure) or crystallisation from another solvent or solvent mixture. The complex may precipitate from the solvent for the reaction either itself or as a mixed salt (e.g., as a metallate with the other ions in the solution). Where the complex is soluble in the solvent for the reaction, it can be separated from any insoluble by-products (if present) by filtration and obtained as a solid by evaporation of the reaction solvent (preferably under reduced pressure). Again, the complex may be purified by sublimation or crystallisation.

To avoid the presence of water molecules in the complex which might provide non-radiative relaxation pathways, the process is preferably carried out under anhydrous conditions. It is also advantageous to exclude oxygen from the reaction mixture by carrying out the process under an inert gas atmosphere e.g., of nitrogen or argon.

The process may be carried out via the following reaction:

wherein

M' is a monovalent metal such as an alkali metal e.g., sodium or potassium, or thallium or silver (as $Tl^+$ and $Ag^+$, respectively)

p,M,Z and L are as defined above, and q is 2-p and A is a counterion.

In a preferred version of the process, two equivalents of $M'ZL_3$ are suspended or dissolved in a solvent and are treated with one equivalent of a divalent lanthanide salt. The reaction mixture is stirred for a period of time between one and 100 hours either at room temperature or at a temperature up to the boiling point of the solvent under standard conditions.

The accompanying drawings illustrate, by way of example only, the present invention. In the drawings.

EXAMPLES

Figure 1:
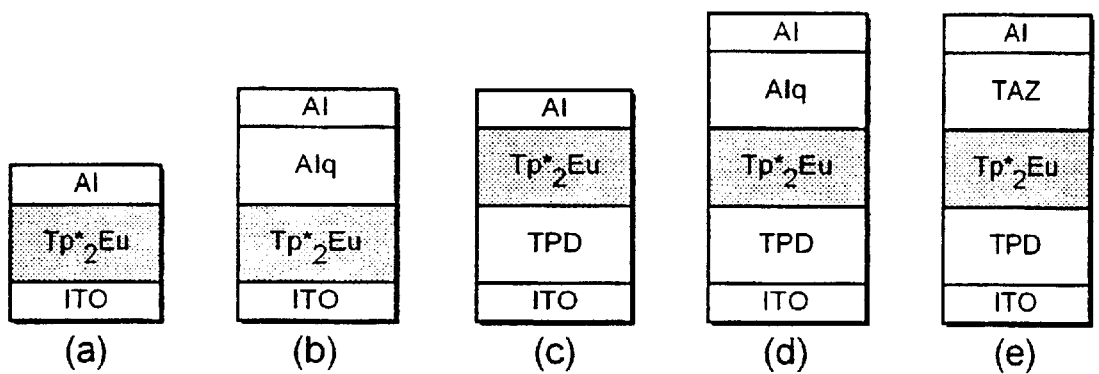
FIG. 1 shows, schematically, the successful and unsuccessful structures used to prepare an EL device according to the invention.

The following compounds are referred to in abbreviated forms as indicated below in the examples.

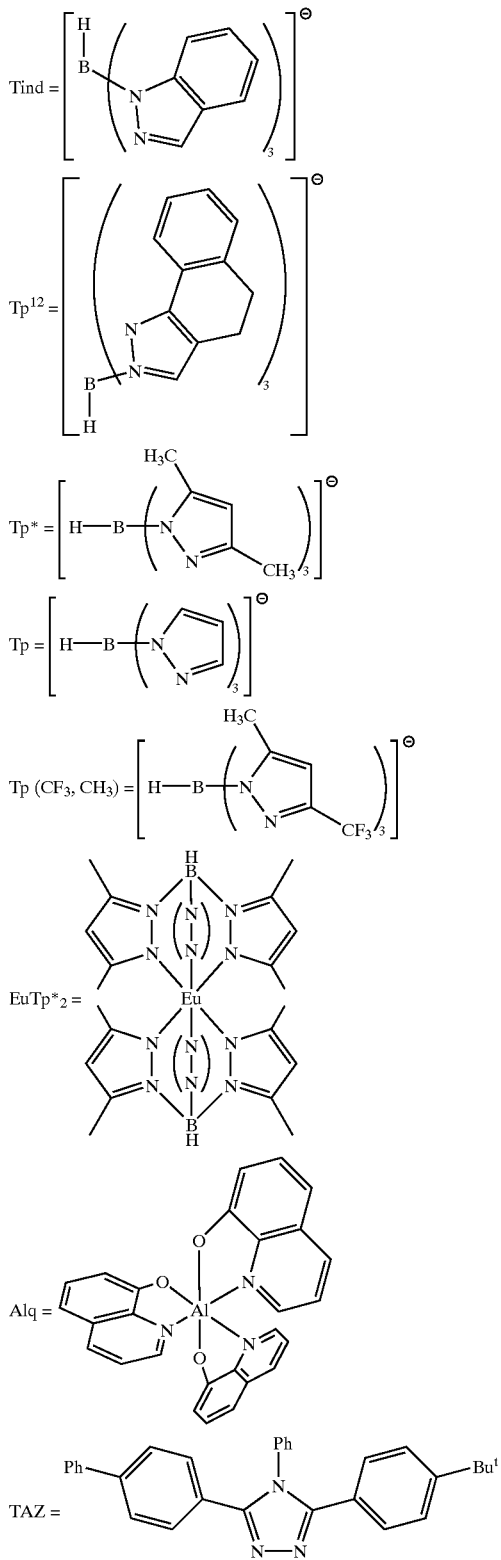

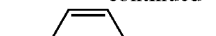

Example 1

Preparation of Bis(tris(dimethylpyrazolyl)borate) europium (II) (EuTp*$_2$)

Bis(tris(dimethylpyrazolyl)borate)europium (II), (Tp*$_2$Eu,1b), was prepared in near quantitative yields by reaction of EuI$_2$(THF)$_2$ with a stoichiometric amount of KTp* (i.e., K[HB(C$_5$H$_7$N$_2$)$_3$]) in THF. The product precipitated from solution as its KI metallate, 1a, as a bright orange powder which was insoluble in all common solvents. Sublimation of 1a in a high vacuum cleaved the metallate affording the homoleptic complex, 1b, as a bright orange microcrystalline powder, soluble in THF. The composition of this paramagnetic material was verified by mass spectroscopy, elemental analysis and comparison of its IR spectrum with that of the structurally analogous Sm(II) derivative. Photoluminescence (PL) measurements of both 1a and 1b at room temperature were identical and showed broad emissions at $\lambda_{max}$ 596 nm (100%) with a full width at half maximum (FWHM) linewidth of 50 nm, and a less intense (5%) emission at $\lambda_{max}$ 430 nm.

A solution of EuI$_2$(THF)$_2$ (1.1 g. 2.0 mmol) in THF (30 ml) was added dropwise to a solution of KTp* (1.33 g, 4.0 mmol) also in THF (30 ml), at room temperature. A bright orange precipitate of the metallated complex formed immediately. The reaction mixture was stirred at room temperature for 6 hours and the solvent removed under reduced pressure. The bright orange residue was washed with THF (2×20 ml) and dried in vacuo, to give the analytically pure metallate (i.e., the 1b adduct with potassium iodide) 1a as a bright orange microcrystalline solid in near quantitative yield (1.83 g, 96%). Sublimation at 100° C. under high vacuum ($10^{-5}$ mtorr) afforded the orange homoleptic complex, 1b, quantitatively. Both 1a and 1b were used without further purification for the EL studies. Anal Calcd for C$_{30}$H$_{44}$B$_2$EuN$_{12}$: C, 48.3: H, 5.94; N, 22.5; Eu, 20.4; B, 2.90; Found: C, 47.4; H, 5.88; N, 22.1; Eu, 19.9; B, 2.98: PL (solid) [nm] 430 (5%), 596 (100%); $\lambda_{max}$ [nm] 216 (100%), 410 (5%); $\nu_{max}$ (nujol) [cm$^{-1}$]; 2526 (m), 1734 (w), 1577 (vs), 1440 (s), 1417 (s), 1365 (s), 1346 (s), 1192 (vs), 1140 (w), 1073 (s), 1037 (s), 986 (m), 829 (m), 697 (m), 667 (w), 654 (m). FAB-MS 747 (3%), 450 (3%), 299 (37%), 203 (100%).

Example 2

SmTP*$_2$

SmI$_2$.2THF (0.45 g, 0.86 mmol) in THF (25 ml) was added dropwise to a stirred solution of KTp* (545 g, 1.64 mmol) in THF (25 ml). A purple insoluble solid was immediately formed. The reaction was only carried out on a speculative scale to investigate any photoluminescence properties.

Example 3

YbTp*$_2$ 1 g (4.1 mmol) of YbCl$_2$ and 2.724 g (8.2 mmol) of KTp* were mixed dry under nitrogen. 50 ml of THF were added resulting in a milky solution which contained grey flakes of $YbCl_2$, this mixture was allowed to stir for 24 hours. After stirring the mixture had become red and appeared to contain a metallic-grey powder. The red solution was filtered and the solvent was removed under vacuum, affording 1.85 g of a pink solid.

Example 4

$EuTind_2$ $EuI_2.2THF$ (1.1 g, 2 mmol) was mixed dry with KTind (1.609 g, 4 mmol) and 50 ml of THF was added with stirring. The mixture immediately became orange and was allowed to stir for 24 hours. Unlike $EuTp*_2$ the product was soluble in THF. The solvent was removed under vacuum and the orange product extracted into $Et_2O$, this extract was stripped of solvent yielding 1.57 g of a dull orange solid.

Example 5

$EuTp^{12}{}_2$ $EuI_2.2THF$ (1.1 g, 2 mmol) and $KTp^{12}$ (2.234 g, 4 mmol) were mixed and 50 ml of THF was added giving a yellow solution, which was allowed to stir overnight. The yellow solution was filtered from a white precipitate (presumably KI) and concentrated and then cooled to −30° C. in an attempt to crystallise the desired product. This process resulted in further precipitation of KI and the solution was again filtered, concentrated and cooled with the same result. Heating the solution lead to a change in colour from yellow to orange, filtering and removal of solvent under vacuum afforded 2.75 g of an orange yellow solid which became brown on standing under argon.

Example 6

$EuTp_2$ $EuI_2.2THF$ (1 g, 1.8 mmol) and KTp (0.917 g, 3.6 mmol) were mixed dry and 50 ml THF added yielding a bright yellow solution which was allowed to stir overnight. Filtration and evaporation of solvent under vacuum afforded a yellow-orange solid.

Yield: 0.95 g

Elemental analysis, calculated for $C_{18}H_{20}B_2EuN_{12}$ (%): C, 37.4; H, 3.5; B, 3.7; Eu, 26.3; N, 29.1. Found: C, 41.1; H, 4.8; N, 23.2; B, 1.7; Eu, 19.4.

The discrepancy in these figures suggest co-ordination of about 3 THF molecules. Problems may have also occurred due to the air sensitivity of the compound.

Example 7

A. Preparation of 3-trifluoromethyl-5-methylpyrazole

To 1,1,1-trifluoro-2,4-pentadione (15.14 g, 98 mmol) in MeOH (200 ml) was added hydrazine monohydrate (4.92 g, 98 mmol) in MeOH (50 ml) and c.HCl (1.3 ml, 32%). The resulting clear solution was allowed to stir for 12 h. Removal of solvent by distillation up to 200° C. yielded a clear oil which crystallised on cooling. These crystals were dissolved in $Et_2O$, dried over $MgSO_4$, filtered and the solvent removed under reduced pressure. The resulting white solid was sublimed at 80° C. and $10^{-2}$ mbar, yielding the pure pyrazole as a white solid (10.91 g, 73 mmol, 74%).

B. Preparation of potassium tris(3-trifluoromethyl-5-methylpyrazolyl)borate ($KTp(CF_3,CH_3)$)

$KBH_4$ (0.58 g, 10.8 mmol) and 3-methyl 5-trifluoromethylpyrazole (5.0 g, 36.8 mmol) were mixed under nitrogen. 5 ml decalin was added under Ar. This mixture was heated with stirring to 180° C. for 3½ h. The resulting white solid was washed with two 25 ml portions of dry hexane and dried in vacuo. The product was then extracted into 50 ml dry THF and filtered. Removal of the THF yielded the pure product (1.155 g, 2.3 mmol, 21%).

NMR data
Proton NMR:
Solvent DMSO-d6
6.24 ppm (1H, s, pyrazole proton)
1.89 ppm (3H, s, $CH_3$)
$^{19}F$ NMR:
−60 ppm (s, $CF_3$)
$^{11}B$ NMR:
solvent $CDCl_3$
−3.5 ppm (d, BH)
mpt~240° C. (decomposed)
IR Nujol mull 2527 $cm^{-1}$
MS 499 (parent ion) matches isotope simulation of m+

C. Preparation of $Eu[Tp(CF_3,CH_3)]_2$

Figure 4:
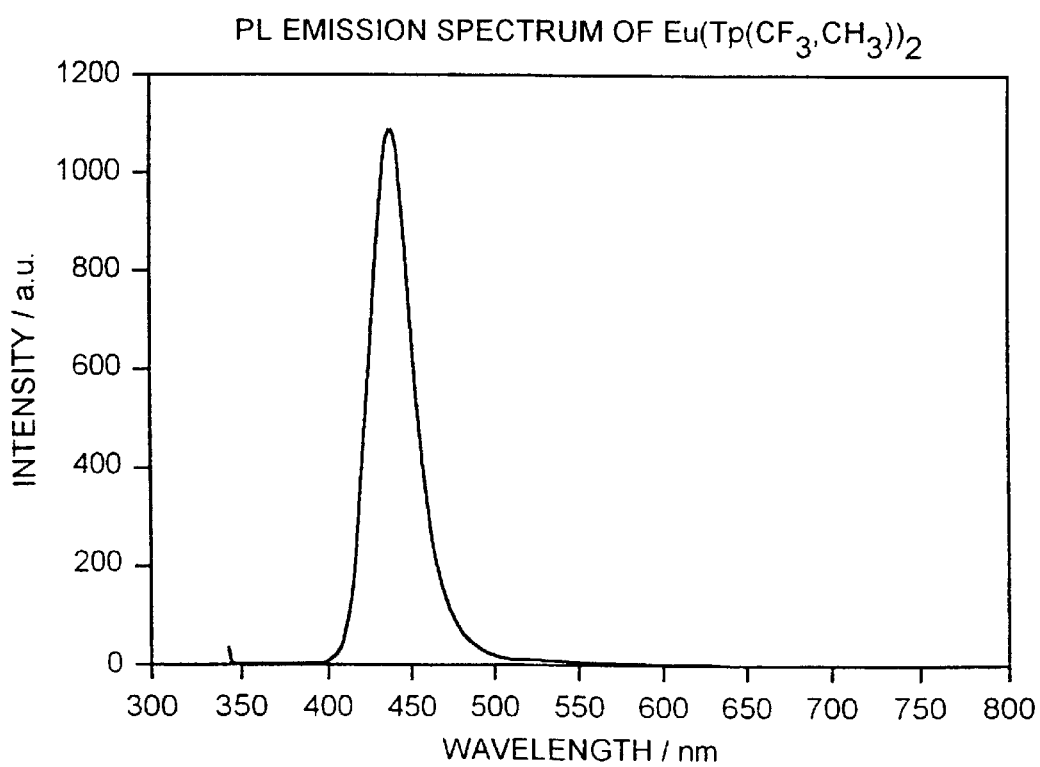
FIG. 4 shows the PL emission spectrum of the complex $Eu[Tp(CF_3,CH_3)]_2$ prepared in Example 7.

The complexes were prepared by reacting 2 equivalents of $KTp(CF_3,CH_3)$ with $EuI_2.THF$ in THF for 24 hours. Then the THF was removed under reduced pressure, the solid residue washed twice with diethyl ether, dried and then sublimed at 220° C. and $10^{-3}$ bar yielding the pure complex. The resulting complex exhibits bright blue luminescence under UV irradiation (FIG. 4).

Example 8

Preparation of Electroluminescent (EL) Device

Low resistance indium-tin-oxide (ITO) coated glass was cut into 1"×1" (2.54 cm×2.54 cm) plates and ultrasonically cleaned for 10 minutes in detergent, deionised water, acetone and methanol and then dried in a stream of dry nitrogen. After cleaning, the substrates were placed inside a vacuum evaporator with a base pressure better than $1×10^{-6}$ torr (1.33 nbar) and the organic layers were sequentially evaporated from Mo boats at a deposition rate of 0.1–0.4 nm/s as measured by a calibrated crystal thickness monitor. Substrates were kept at room temperature throughout the evaporation. After deposition of the organic layers, the structures were transferred to a second evaporator where an array of 0.5 mm diameter Al contacts were evaporated through a shadow mask to a thickness of 150 nm.

All electrical testing and optical measurements were performed under ambient conditions with no protective coating applied to the devices. EL measurements were made under forward bias (ITO positive) and the emission output was viewed in the forward direction through the transparent ITO electrode. The current-voltage (I-V) characteristics were measured with a Thurlby-Thandar TSX3510P programmable DC power supply and a Keithley 617 programmable electrometer both controlled by IBM compatible PC via IEEE488 interface. EL characteristics of devices including the spectral and power dependencies of light output were measured with a LOT-Oriel Instaspec™ IV charge-coupled device (CCD) detector attached to an Oriel Multispec™ ⅛ M spectrograph with 400 lines/mm ruled grating. A fibre linked sighting optics was used to focus the image of the device to the entrance of spectrograph. The system was calibrated with an Oriel 200 W QTH calibrated lamp connected to an Oriel 300 W radiometric power supply. Values of radiance and luminance were also measured with an International Light IL1700 Research Radiometer equipped with a calibrated Si photodetector. Solution PL spectra were recorded using a Perkin-Elmer LS50B spectrophotometer. IR spectra were recorded using a Perkin-Elmer 1710 FTIR spectrometer as nujol mulls between KBr plates. Solution UV-vis spectra were recorded using a Perkin-Elmer Lambda-19 UV-vis NIR spectrometer as THF solutions.

Both 1a and 1b were evaporated to form thin films without any noticeable difference in device properties. Consequently, all devices were prepared from 1a because of synthetic ease. Several device structures were prepared to establish the thin film properties of 1a.

Figure 2:
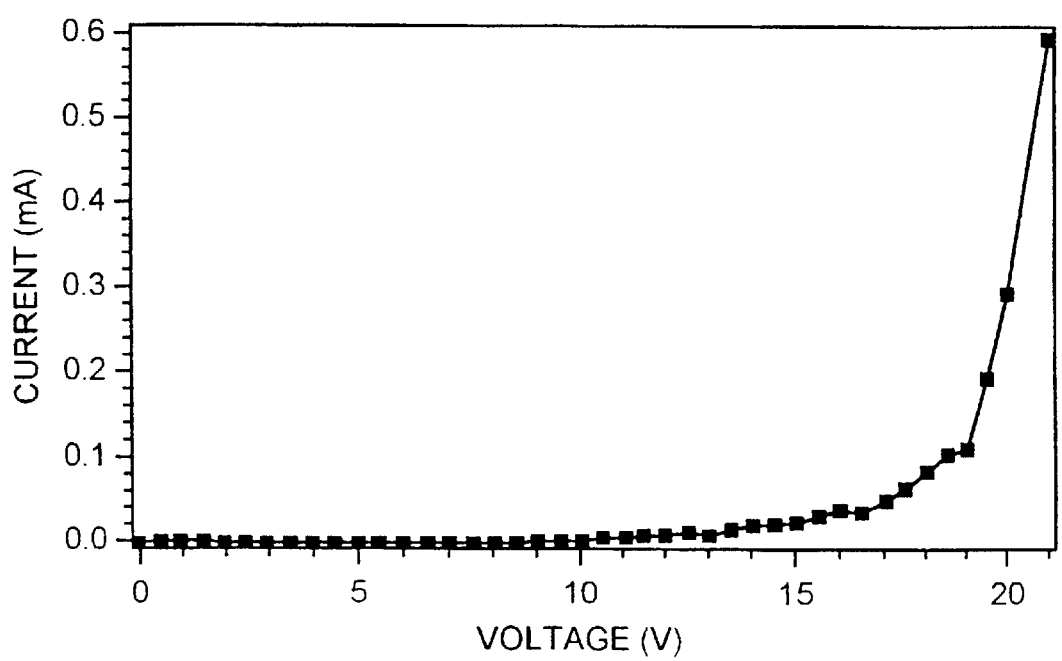
FIG. 2 is a graph of the current-voltage characteristics of a device according to the invention.

Single and double layer structures without a hole transporting layer (HTL) (FIG. 1b) failed to produce any EL. Introduction of an HTL (N,N'-diphenyl-N-N'-bis-(3-methyl)-1,1'-biphenyl-4,4'-diamine) (TPD)) into a single layer device of 1b (FIG. 1c) resulted in weak EL with broad components in the blue and orange regions of the visible spectrum. This is consistent with charge recombination at the TPD/1b heterojunction interface. Multilayer structures containing both TPD and tris(8-quinolato-N,O)aluminium (III) (Alq) (FIG. 1d) exhibited EL with orange and green components, suggesting charge recombination in both the Alq and 1b layers. As the thickness of the Alq layer decreased, the intensity of the green emission also decreased. Since charge transport through the phosphor layer into the ETL appeared to be occurring and this was reducing the device efficiency, the structure was modified to include an ETL with hole blocking properties (FIG. 1e). This method has been reported by others to be an efficient method of improving EL in devices where charge transport through layers is a problem. Accordingly, in our system we observed improved device performance when 3-(4-biphenylyl)-4-phenyl-5-(4-tert-butylphenyl)-1,2,4-triazole (TAZ) was used as such a layer. The optimum device structure tested in this work was found to consist of a 10 nm layer of 1b evaporated onto an ITO substrate previously coated with a 40 nm layer of TPD, also by evaporation. A 20 nm layer of TAZ was evaporated on top of the 1b layer and the cathodic contact was made by evaporating a layer of Al on top of the TAZ. A typical current-voltage characteristic for this device is shown in FIG. 2.

Figure 3:
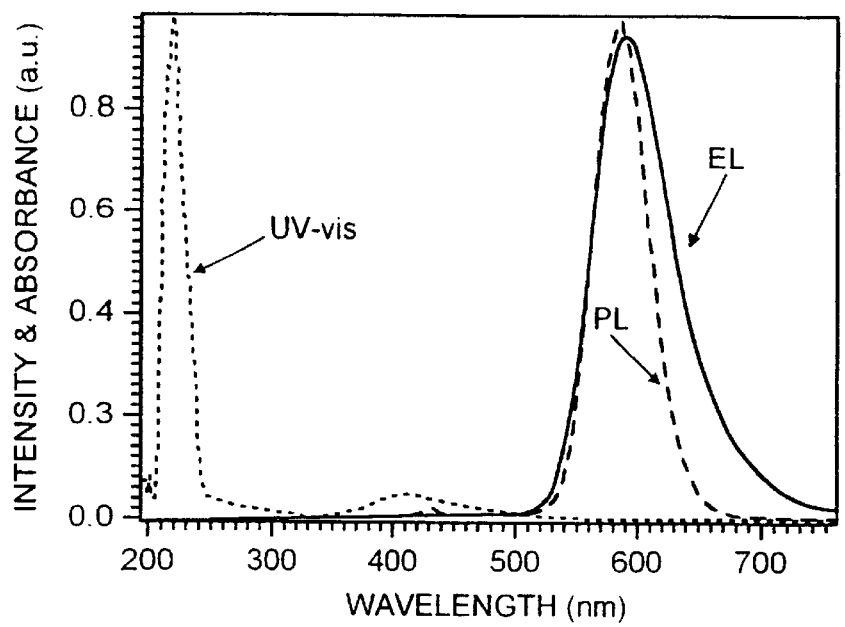
FIG. 3 shows the spectra of UV-vis absorption and photoluminescence for a complex of the invention together with the EL spectrum for the same complex in an EL device of the invention.

The EL spectrum for the emission from the device is given in FIG. 3. This figure also shows the spectra of UV-vis absorption and photoluminescence of 1b.

Under these conditions, the device exhibited orange electroluminescence (FIG. 3) with a maximum luminance of 10 cd/m$^2$ at a current density of 20 mA/cm$^2$, this corresponds to an external quantum efficiency of 0.01% and is comparable to that seen in other molecular lanthanide based devices. The 1931 CIE coordinates of the emission were x=0.5418 and y=0.4500. The luminance was directly proportional to the current between 0.075 mA and 0.5 mA. The EL spectrum of the device closely matches the PL spectrum of 1b suggesting that emission arises from the europium complex. The EL spectrum is also noticeably broadened on the long wavelength side of the emission. Such features are normally associated with the formation of an exciplex or heterogeneities either in the emissive layer or at layer junctions and may in this case arise from a TPD/1b interaction at the heterostructure interface in the device.

The new divalent organolanthanide complexes provided by the present invention offer promise as tunable volatile phosphors for thin film devices.

What is claimed is:

1. Light emitting device comprising a complex containing a divalent lanthanide metal cation complexed with from one to three polydentate ligands.

2. Device as claimed in claim 1, wherein each ligand comprises one or more pyrazolyl groups, optionally substituted and optionally fused with a substituted or unsubstituted, heterocyclic or carbocyclic, aromatic or non-aromatic, ring system, one of the nitrogen atoms of the pyrazolyl groups forming a coordinate bond to the metal.

3. Device as claimed in claim 1 or claim 2, wherein the ligands are trispyrazolylborate anions, the pyrazolyl groups being optionally substituted and optionally fused with a substituted or unsubstituted, heterocyclic or carbocyclic, aromatic or non-aromatic, ring system, optionally substituted at the boron atom.

4. Device as claimed in claim 1, wherein the complex has the formula (I):

$$[(Z(L)_3)_pM]A_q \qquad (I)$$

wherein

Z is a carbon atom or R'—B fragment p is 1 or 2 q is 2-p and

A is a counterion

R1 is: (i) hydrogen, aryl or aralkyl each optionally substituted with from one to five halogen or $C_1$ to $C_6$ alkyl groups; or (ii) $C_1$ to $C_6$ alkyl, $C_2$ to $C_6$ alkenyl or $C_2$ to $C_6$ alkynyl each optionally substituted with one or more halogen atoms each L is covalently bound to Z and is independently selected from a group of the formula (II) or (III)

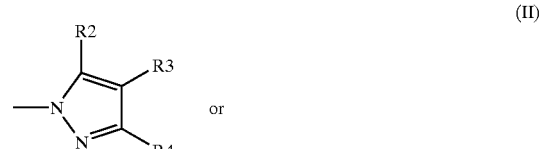

(II)

(III)

in which R$^2$, R$^3$ and R$^4$ are independently selected from: (i) halogen, cyano, nitro, sulphono, amino, $C_1$ to $C_6$ alkylamino, $C_1$ to $C_6$ alkylamido, carboxyl, $C_1$ to $C_6$ alkyloxycarbonyl, hydroxy, $C_1$ to $C_6$ alkoxy, $C_1$ to $C_6$ alkylcarbonyloxy, $C_1$ to $C_6$ alkylcarbonyl $C_1$ to $C_6$ haloalkoxy and hydrogen; (ii) aryl or aralkyl each optionally substituted on the aryl ring or, for aralkyl, on the alkylene chain with from one or more of the groups mentioned under (i) above; and (iii) $C_1$ to $C_6$ alkyl, $C_2$ to $C_6$ alkenyl or $C_2$ to $C_6$ alkynyl each optionally substituted with one or more of the groups mentioned under (i) and (ii) above or either R$^2$ and R$^3$ or R$^3$ and R$^4$ are linked so as to form a fused aromatic or non-aromatic, ring system with the pyrazolyl ring of L and M is a divalent lanthanide metal ion wherein the lanthanide metal is Eu, Sm or Yb.

5. Device as claimed in claim 1, wherein M is Eu.

6. Device as claimed in claim 4 or claim 5, wherein R$^4$ and/or R$^2$ is —(CX$_2$)$_n$X, wherein n is 0 or a positive integer from 1 to 6 and X is halogen, or orthohalogenated or orthodiperhalomethylated aryl.

7. Device as claimed in claim 6, wherein $R^4$ and/or $R^2$ is trifluoromethyl.

8. Device as claimed in claim 4 or claim 5, wherein $R^4$ and $R^2$ are both methyl.

9. Device as claimed in claim 4, wherein $R^3$ is hydrogen.

10. Device as claimed in claim 4, wherein Z is H—B.

11. Device as claimed in claim 4, wherein p is 2 and q is 0.

12. A device as claimed in claim 4 wherein the complex has the formula I in which Z is H—B and at least one of the L groups is a pyrazolyl group of formula II or III in which at least one of $R^2$, $R^3$ and $R^4$ is a trifluoromethyl group.

13. A device as claimed in claim 12, wherein for each L group one of $R^2$ and $R^4$ is a trifluoromethyl group and the other is selected from $C_1$–$C_6$ alkyl, $C_2$–$C_6$ alkenyl, $C_2$–$C_6$ alkynyl, aryl and aralkyl, $R^3$ is H and M is Eu.

14. A device as claimed in claim 1 which is a flat panel display.

15. An organometallic complex having the formula (I)

wherein

Z, p, $R^1$, $R^2$, $R^3$, $R^4$, L, A, q and M are as defined in claim 4, provided that when p is 2 and Z is HB:
(i) when $R^3$ is hydrogen, $R^2$ and $R^4$ are not both hydrogen or both methyl;
(ii) when $R^3$ is hydrogen and one of $R^2$ and $R^4$ is hydrogen, the other is not phenyl or 2'-thienyl; and
(iii) when $R^2$ is methyl and $R^3$ is hydrogen, $R^4$ is not —C(CH$_3$)$_3$.

16. A complex as claimed in claim 15, wherein M is Eu.

17. A complex as claimed in either claim 15 or claim 16, wherein Z is H—B.

18. A complex as claimed in claim 15, wherein $ZL_3$ is

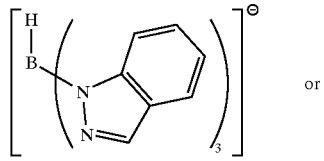 or

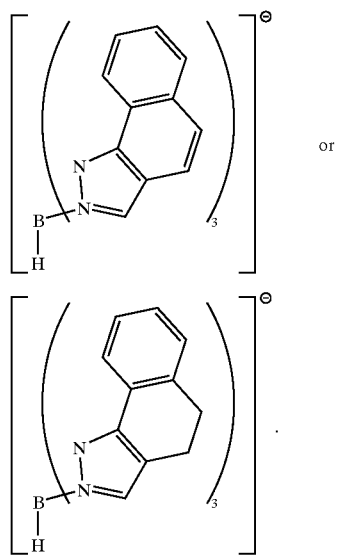

19. A complex as claimed in claim 15, wherein p is 2 and q is 0.

20. A complex as claimed in claim 15, wherein Z is H—B and at least one of the L groups is a pyrazolyl group of formula II or III in which at least one of $R^2$, $R^3$ and $R^4$ is a trifluoromethyl group.

21. A complex as claimed in claim 20, wherein in each L group one of $R^2$ and $R^4$ is a trifluoromethyl group and the other is selected from $C_1$–$C_6$ alkyl, $C_2$–$C_6$ alkenyl, $C_2$–$C_6$ alkynyl, aryl and aralkyl, $R^3$ is H and M is Eu.

22. A process for producing the complex of claim 15 comprising the steps of reacting $M^{2+}$ ions with $ZL_3$ ions in solution and separating the complex from the reaction mixture.

23. A process as claimed in claim 22 which is carried out under substantially anhydrous conditions.

* * * * *